United States Patent [19]
Peterson

[11] 4,024,159
[45] May 17, 1977

[54] PROCESS FOR THE PRODUCTION OF LIQUID ACETALS

[75] Inventor: Marvin L. Peterson, Woodstown, N.J.

[73] Assignee: E. I. Du Pont de Nemours and Company, Wilmington, Del.

[22] Filed: Aug. 7, 1974

[21] Appl. No.: 495,510

[52] U.S. Cl. .......................... 260/340.7; 260/615 A
[51] Int. Cl.² ........................................ C07D 319/06
[58] Field of Search ............. 260/340.7 (U.S. only), 260/615 A

[56] References Cited

UNITED STATES PATENTS

| | | | |
|---|---|---|---|
| 1,837,273 | 12/1931 | Knorr et al. | 260/340.7 |
| 2,272,153 | 2/1942 | Moyle | 260/340.7 |
| 2,388,409 | 11/1945 | Harvey | 260/615 A |
| 2,401,336 | 6/1946 | Calder et al. | 260/340.7 UX |
| 2,432,601 | 12/1947 | Wiley | 260/340.7 X |
| 2,879,305 | 3/1959 | Pasedach et al. | 260/340.7 X |

*Primary Examiner*—Anton H. Sutto

[57] ABSTRACT

Alcohols and/or alpha, beta or alpha, gamma diols having at least four carbon atoms are reacted with aldehyde or dialdehyde compounds at a temperature ranging from 0° – 100° C in the presence of an acid catalyst to produce an organic-aqueous two-phase liquid product containing the acetal in the organic phase.

7 Claims, No Drawings

PROCESS FOR THE PRODUCTION OF LIQUID ACETALS

BACKGROUND OF THE INVENTION

Many patents disclose conditions for converting aldehydes to acetals. For example, U.S. Pat. No. 2,131,998 discloses the addition of an alcohol to a double bond as well as acetal formation, i.e.,

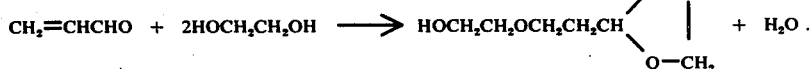

U.S. Pat. No. 2,566,559 discloses the use of a fixed bed cation exchange resin as a catalyst for the preparation of acetals and U.S. Pat. No. 2,840,615 discloses the use of strongly acidic cation exchange resins as catalysts for acetal formation from methanol and acetaldehyde. U.S. Pat. No. 2,678,950 discloses the use of sulfo acid catalysts with continuous removal of water from the reaction mixture and U.S. Pat. No. 3,014,924 discloses the use of highly porous silica-alumina catalysts impregnated with a small quantity of a strong mineral acid. U.S. Pat. No. 2,987,524 discloses the preparation of cyclic unsaturated acetals using a sulfo acid catalyst with continuous removal of water. U.S. Pat. No. 2,729,650 discloses the preparation of unsaturated cyclic acetals using inorganic salts as catalysts.

The reactions of alcohols with aldehydes to form acetals are equilibrium reactions. The degree of conversion to the acetal is limited by the equilibrium constant for the reaction, unless one of the products can be removed from the reaction site.

$$\text{alcohol} + \text{aldehyde} \rightleftharpoons H_2O + \text{acetal}$$

$$K = \frac{C_{H_2O} \cdot C_{acetal}}{C_{alcohol} C_{aldehyde}}$$

K is the equilibrium constant, and the various C's represent the molar concentrations of reactants and products. The equilibrium constant for the reaction of methanol with acetaldehyde allows only about a 50% conversion to acetal while the reaction of acrolein with 2-methyl-1,3-propanediol (MPD) yields only 65% of acetal under equilibrium conditions.

Several techniques have been used in an attempt to obtain conversions of reactants to acetals at concentrations higher than the equilibrium concentration. The most common technique used is the completion of the reaction by azeotropic distillation of water with a water-insoluble organic solvent such as benzene or toluene as disclosed in U.S. Pat. No. 2,987,524. Such a process suffers from several basic deficiencies. The overall efficiency is low because low yields of acetal are obtained per volume of reactor space, a high energy consumption is needed for the azeotropic distillation, acetal product must be separated by distillation from the solvent, the cost of solvent adds to the process cost and at the temperatures and times required for azeotropic distillation, unsaturated aldehydes, such as acrolein, react to form side products by polymerization and addition of water and alcohols to the carbon-carbon double bond.

Large excesses of one reactant, usually the alcohol, have been used to drive the equilibrium toward higher conversions with more complete utilization of the aldehyde. U.S. Pat. No. 2,566,559 teaches the preferred use of 4 to 5 moles of alcohol per mole of aldehyde. The acetal product must be separated from the large excess of alcohol, and the alcohol recovered and recycled to the process. High molar ratios of aldehyde/alcohol may be used, but side polymerization reactions and additions to the double bond may consume some of the unsaturated aldehydes.

Water has also been removed from the reaction by dessicants, such as calcium chloride as disclosed in German Patent 434,989. These systems are difficult to handle and costly to operate, because the dessicant must be recovered, dried and returned to the process.

SUMMARY OF THE INVENTION

It has now been found that liquid acetals having a solubility of less than 10% by weight in water at 25° C can be prepared at higher than equilibrium concentration yields by reacting an alcohol and/or diol having at least four carbon atoms and a maximum of three carbon atoms separating the diol hydroxyl groups, (alpha, beta or alpha, gamma diols) at a temperature ranging from 0°–100° C in the presence of an acid catalyst, with at least a stoichiometrically equivalent quantity of an aldehyde and/or dialdehyde. A two-phase aqueous-organic liquid product is obtained in which the acetal is contained in the organic phase. The aldehyde and/or dialdehyde is generally a saturated or unsaturated alkyl ($C_1$-$C_{20}$), alkaryl ($C_7$-$C_{20}$) or aralkyl ($C_7$-$C_{20}$) compound which may contain chlorine, bromine, alkyl ($C_1$-$C_{10}$), aryl (phenyl, naphthyl), carbalkoxy ($C_1$-$C_{10}$ in alkoxy), alkoxy ($C_1$-$C_{10}$) and the like substituents which will not solubilize the organic-acetal layers or interfere with the alcohol-aldehyde reaction. The alkyl group may be cycloalkyl and the aryl groups in the alkaryl and aralkyl groups are generally phenyl or naphthyl.

Because of the formation of two distinct layers, the reaction product in the organic phase is effectively removed from the reactants in the aqueous phase before equilibrium is reached. Thus, higher conversions to acetal and higher yields are obtained than had been possible heretofore. The process is particularly effective for preparing acetals having six-membered rings (1,3-dioxanes) from 1,3-diols and aldehydes since the stability of the six-membered ring promotes a higher conversion to acetal before equilibrium is reached. The surprisingly low solubility of water in such acetals and vice versa favors layer separation.

The present process is also advantageous since it does not require large excesses of reactants that must be recovered, solvents that must be recovered, dessicating agents or azeotropic distillation of water with high energy consumption.

DETAILED DESCRIPTION OF THE INVENTION

As used herein, the term alcohol is intended to include alpha, beta and alpha, gamma diols and the term aldehyde is intended to include dialdehydes and mixtures of each.

Any alcohol having at least four carbon atoms may be used in the practice of this invention. Compounds containing three or more hydroxyl groups cannot be used because the additional alcohol functional groups tend to solubilize the system so that the distinct organic-aqueous phases to not form. Conversions to acetal increase with increasing chain length of the alcohol. Preferably, however, the alcohol should contain a maximum of 20 carbon atoms in either a straight or branched chain since a large number of carbon atoms might result in a solid acetal product. Some specific alcohols which may be used include, for example, 2-methyl-1,3-propanediol, 1,3-butanediol, 2,4-pentanediol, 2,2-dimethyl-1,3-propanediol, 2-ethyl-1,3-propanediol, 2-methyl-2,4-pentanediol, 1,3-pentanediol, 2,4-hexanediol, 1,3-hexanediol, 2,2-diethyl-1,3-propanediol, 1,3-heptanediol, 2,4- or 3,5-heptanediol, 2,3-butanediol, 2,3-dimethyl-2,3-butanediol, 2,3-diethyl-2,3-butanediol, butyl, amyl, hexyl, heptyl, octyl, decyl, lauryl, myristyl, stearyl, crotyl, benzyl, cinnamyl, isobutyl, isoamyl, 4-methyl-1-pentanol, 3-methyl-1-pentanol, 2,3-dimethyl-1-pentanol, 2-ethyl-1-hexanol, 2-phenyl-1-ethanol and the like alcohols and mixtures thereof. Any alcohols containing hetero atoms such as oxygen, sulfur, carbonate and the like atoms or groups in the hydrocarbon structure may also be used as well as those containing substituents such as alkoxy ($C_1$-$C_4$), aryloxy (benzoxy, naphthoxy), halogen (chlorine, fluorine, bromine, iodine), —$NO_2$, —SH and the like. Some examples of such alcohols include 4-chloro-1-butanol, 4-bromo-1-butanol, 3,4, or 5-chloro-1-pentanol, 4-iodo-1-butanol, 2-ethoxy-1-ethanol, 3-methoxy-1-propanol, 4-methoxy-1-butanol, 2-butoxy-1-ethanol, 3-butylthio-1-propanol, 4-methylthio-1-butanol, 3-acetoxy-1-propanol, 4-acetoxy-1-butanol, 3-nitro-1-butanol, furfuryl alcohol, 3-benzoxy-1-propanol, 2-benzoxy-1-ethanol, 2-naphthoxy-1-ethanol, 4-nitro-1-butanol, 2-(p-nitrophenoxy)-1-ethanol, p-chlorobenzyl alcohol and the like and mixtures thereof.

The process of the invention may be used to prepare acetals of any cyclic or acyclic, saturated or unsaturated aliphatic or aromatic aldehyde that reacts with an alcohol having four or more carbon atoms to yield an acetal which has a solubility of less than 10% by weight in water at 25° C. Suitable aldehydes range from saturated aldehydes prepared from formaldehyde to the long carbon chain aldehydes and dialdehydes. High molecular weight and/or solid aldehydes may be used if they are soluble in the alcohol or any medium used for reaction with the alcohol. The process of the invention is particularly suited to the preparation of acetals from unsaturated aldehydes, such as acrolein, because the reaction conditions are mild so that unwanted side reactions do not occur. The aldehyde or dialdehyde may also contain the same substituents described above for the alcohols or diols. Some specific examples of suitable aldehydes and dialdehydes include formaldehyde, acetaldehyde, propionaldehyde, butyraldehyde, valeraldehyde, isobutyraldehyde, isovaleraldehyde, caproaldehyde, heptaldehyde, octaldehyde, capric aldehyde, stearaldehyde, acrolein, crotonaldehyde, benzaldehyde, furfural, glyoxal, phenylpropargylaldehyde, 3-penten-1-al, 2-penten-1-al, 3-methyl-2-penten-1-al, cinnamaldehyde, p-chlorbenzaldehyde, p-bromobenzaldehyde, m-nitrobenzaldehyde, p-fluorobenzaldehyde, p-methoxybenzaldehyde, o-methoxybenzaldehyde, naphthaldehyde, g-acetoxybutyraldehyde, diethyl a-formylsuccinate, formylcyclopentane, trimethylacetaldehyde, ethyl glyoxylate, chloroacetaldehyde, 3-bromopropionaldehyde, terephthalaldehyde, ethyl p-formylbenzoate, and the like and mixtures thereof.

The alcohol should be reacted with the aldehyde in stoichiometric proportions for best results although as much as a 50% excess of the aldehyde may be employed. Higher concentrations of aldehyde or greater than stoichiometric equivalent amounts of alcohol tend to solubilize the system and prevent phase separation. In addition, great excesses of unsaturated aldehyde or dialdehyde result in by-product formation via reaction across the double bond. Preferably, 1 equivalent of alcohol or diol to a range of 1–1.5 equivalents of aldehyde or dialdehyde is used.

Generally, the reactants are miscible liquids or else one is soluble in the other so that no solvent need be employed in carrying out the reaction. Therefore, the alcohol and aldehyde each may be introduced to the reaction per se or, if desired, they may be introduced in aqueous solution. However, since too high a concentration of water may cause solubility problems, the medium in which the reaction is carried out should contain only 0 to 10% by weight of water based on the weight of the alcohol or diol and aldehyde or dialdehyde. However, any amount of water which can be handled easily in the reactor and during separation of the two phases may be employed.

The reactions of the process of this invention are acid-catalyzed and conventional acid catalysts may be used. Soluble mineral acids, such as hydrochloric acid, sulfuric acid and phosphoric acid catalyze the reaction strongly. Organic sulfonic acids, such as p-toluenesulfonic acid, and are also excellent catalysts. Reaction mixtures employing these soluble catalysts are homogeneous until separation of phases begins. The disadvantage of using soluble catalysts is that they must be neutralized before further processing of the reaction product to avoid product hydrolysis during work up. Therefore, in a preferred embodiment of this invention, insoluble, heterogeneous catalysts of the strongly acidic cationic exchange resin type are used. These catalysts are advantageous because they are easily separated from reaction product and a neutral reaction product is produced. They have a long life and may be used repeatedly. The resins may be used either in a stirred slurry system or as a fixed bed catalyst through which the reactants are passed.

Any strongly acidic water insoluble ion exchange resin can be used in the practice of this invention. Typical such resins are those containing sulfonic acid groups such as the resins disclosed in U.S. Pat. 2,366,007 issued Dec. 26, 1944 to G. F. D'Alelio which include sulfonated styrene-divinyl benzene copolymers commercially available as Dowex, Amberlite and the like resins. Other suitable cation-exchange resins include, for example, the phenol sulfonic acid-formaldehyde reaction products.

Any suitable reactor may be used to carry out the reaction including a simple pot. Generally, however, for continuous reactions, a reactor with a fixed catalyst bed of an insoluble strongly acidic ion exchange resin through which the reactants are passed is preferred.

The temperature of the reactor may vary from 0° to 100° C with a preferred temperature range from 25° to 50° C. The best temperature in each case will be determined by the reactants used. At temperatures lower than 25° C, the reaction may be too slow to be commercial. At temperatures above 50° C, unsaturated aldehydes such as acrolein tend to undergo side reactions.

Any apparatus may be employed which can be used conveniently to separate the organic from the aqueous phase after the reaction is completed. Since the process of this invention may be carried out either batchwise or continuously, phase separation may also be achieved either batchwise or on a continuous basis. In a batch process, the reaction layers will be separated by draining the lower aqueous layer from the acetal layer in a separating funnel or similar larger scale commercial equipment. In a continuous process, the reaction products will be fed to a decanter which continuously separates the layers.

The invention is further illustrated but is not intended to be limited by the following examples in which all parts and percentages are by weight unless otherwise specified.

EXAMPLE 1

2-vinyl-5-methyl-1,3-dioxane (VMD)

A mixture of 1 molar equivalent of 2-methyl-1,3-propanediol (MPD) and 1.1 molar eq. of acrolein was passed through a column (¼ inch × 6 inches) of 10 ml. of strongly acidic cationic exchange resin (Dowex MSC-1) at the rate of 0.55 g./min. The bed was cooled with circulating water at 25° C and the maximum temperature in the resin bed was 35° C. The reaction product (30.7 g.) divided into 2 layers — an acetal layer (26.6 g.) and an aqueous layer (4.1 g.). The layers were each analyzed by gas-liquid phase chromatography. The acetal layer contained 79% VMD, 3% MPD, 8% acrolein and 3% water. The aqueous phase containing 61% water, 22% MPD, 8% acetal and 4% acrolein. Eighty-three percent of the MPD was converted to acetal. The yield based on acrolein reacted was 96%.

A similar reaction between MPD and acrolein was carried out at a rate of 1.32 g./min. The maximum temperature observed in the resin bed was 48° C. The reaction product (30.7 g.) divided into an acetal phase (26.3 g.) and an aqueous phase (4.4 g.). Conversion of MPD to acetal was 82%. The compositions of the two layers were similar to those above.

For the sake of comparison, a mixture of 0.5 mole 1,3-propanediol and 0.55 mole acrolein were reacted at 50° C in the presence of 0.3 g. p-toluenesulfonic acid. Layers did not separate until the reaction mixture was cooled to 26° C. The mixture gave 18 g. of an aqueous layer which contained about 40% diol, 21% acrolein, 10% 2-vinyl-1,3-dioxane and 25% water. The acetal layer of 49 g. contained 63% 2-vinyl-1,3-dioxane, 23% acrolein, 8% diol and 5% water, conversion to acetal was about 60% which represents only a negligible increase over equilibrium conversion.

EXAMPLE 2

The addition of 0.05 ml. of 37% hydrochloric acid to a mixture of 18.02 g. (0.20 moles) of 2-methyl-1,3-propanediol and 12.12 g. (0.216 moles) acrolein at 30° C produced a rapid temperature rise to 48° C. The temperature was reduced to 30° C and maintained at that temperature for 2 hours with cooling. The reaction mixture divided into 2 layers — 25.62 g. of acetal layer and 4.84 g. of aqueous layer. The conversion to acetal was 89%, of which 98.8% was in the acetal layer. The acetal layer contained 88% of VMD, 14% water, 6.8% acrolein and no diol. The water layer contained 5% of VMD, 21% diol, 62.6% water and 3.8% acrolein.

EXAMPLE 3

The reaction of 26 g. (0.25 mole) of 2,2-dimethyl-1,3-propanediol and 15.4 g. (0.275 mole) of acrolein was catalyzed with 0.1 ml. of 37% hydrochloric acid. At a controlled reaction temperature of 35°–40° C, separation into 2 layers began within 2 minutes. The conversion to acetal was 92%. A similar reaction at 27° C produced 2 layers in 40 minutes and gave the same conversion to acetal. The acetal layer contained 87.7% of 2-vinyl-5,5-dimethyl-1,3-dioxane (VDD), 1.0% diol, 1.0% water and 3.5% acrolein. The water layer contained 1.0% of VDD, 18% diol, 1% acrolein and 77% water.

EXAMPLE 4

A mixture of 1 molar equivalent of 2,2-dimethyl-1,3-propanediol, 1.1 molar equivalents of acrolein and 1 molar equivalent of water was passed through a column (¾ inch × 4 inches) of 40 ml. of strongly acidic cation exchange resin (Dowex MSC-1) at the rate of 5 g./min. The maximum temperature in the resin bed was 55° C when the bed was cooled by circulating water at 25° C. A sample of 91.8 g. of reactor effluent separated into 2 layers — an acetal layer of 71.4 g. and an aqueous layer of 20.3 g. The acetal layer was composed of 88.8% acetal (VDD) and small amounts of diol, 4% acrolein, 3% water and by-products. The aqueous layer was 83.1% water, 13.7% diol, 2.2% acetal and 1.8% acrolein. Conversion to acetal was 89%.

EXAMPLE 5

In this example, 2.0 molar equivalents of water were used with 1.0 molar equivalent of 2,2-dimethyl-1,3-propanediol, and 1.1 equivalents of acrolein. The resin bed was the same one used in the previous example. At a flow rate of 2.7 g./min. and with cooling, the maximum temperature in the resin bed was 30° C. A sample of 100.8 g. separated into 65.4 g. of acetal layer and 35.4 g. of aqueous layer. The conversion to acetal was 82%. The acetal layer contained 89.2% of VDD, 0.4% diol, 1.2% water and 5% acrolein. The aqueous layer contained 3% of VDD, 14% diol, 80% water and 2% acrolein.

Example 6

A mixture of 1.0 molar equivalent of 1,3-butanediol and 1.15 molar equivalents of acrolein was passed through a bed of 10 ml. of the ion exchange resin of Example 1 (50–100 mesh) at the rate of 0.65 g./min. The maximum temperature in the resin bed with cooling was 52° C. A reactor effluent of 104.4 g. separated into 88.5 g. acetal layer and 15.9 g. aqueous layer. The conversion to 2-vinyl-4-methyl-1,3-dioxane was 88%. The acetal layer contained 85.2% of 2-vinyl-4-methyl-1,3-dioxane, 2.7% diol, 3.3% water and 6.7% acrolein. The aqueous layer contained 8.6% of 2-vinyl-4-methyl-1,3-dioxane, 66.8% water, 20.9% diol and 6.2% acrolein.

EXAMPLE 7

A mixture of 0.50 mole 2-methyl-2,4-pentanediol, 0.55 mole acrolein and 0.2 g. polyphosphoric acid reacted at 50° C to form 2 layers within 20 minutes.

The conversion to acetal was 92%. The acetal layer contained 90.5% of 2-vinyl-4,4,6-trimethyl-1,3-dioxane, 6% acrolein, 2% diol and 1.5% water. The aqueous layer contained 3.6% acrolein, <1% of 2-vinyl-4,4,6-trimethyl-1,3-dioxane and 75% water.

EXAMPLE 8

A mixture of 0.2 mole 1,3-butanediol and 0.2 mole acetaldehyde was stirred over 1.0 g. of the resin of Example 1 at 45°–75° C with no heating applied. The reaction mixture separated into 21.0 g. of acetal layer and 3.5 g. of water layer. Conversion to acetal (2,4-dimethyl-1,3-dioxane) was 90%. The acetal layer contained 96% of 2,4-dimethyl-1,3-dioxane, 1.3% diol, 0.6% acetaldehyde and 2% $H_2O$. The aqueous layer contained 41.5% water, 0.8% acetaldehyde, 22% diol and 32% 2,4-dimethyl-1,3-dioxane.

EXAMPLE 9

A mixture of 0.4 mole n-amyl alcohol, 11.6 g. of propionaldehyde, and 0.1 mole of 37% hydrochloric acid was reacted at 35°–40° C. Two layers formed within 5 minutes. Separation of layers gave 45.2 g. of acetal layer (composition — 6% propionaldehyde, 23% amyl alcohol and 70% acetal). The conversion to acetal was 72%.

EXAMPLE 10

A mixture of 0.6 mole n-butyl alcohol, 0.3 mole acetaldehyde and 0.1 ml. 37% hydrochloric acid was reacted at 45°–50° C. Separation into two layers occurred in 1 minute. The aqueous layer was 1.7 g. The conversion to acetal was 66–69%. The acetal layer contained 67.5% of acetaldehyde, di-n-butanal acetal, 26% n-butyl alcohol and 6% acetaldehyde.

EXAMPLE 11

This example shows the effect of excess diol.

A mixture of 4.50 g. (0.050 mole) of 2-methyl-1,3-propanediol and 1.73 g. (0.030 mole) of acrolein with 0.01 g. p-toluenesulfonic acid was reacted at 40°–50° C. The reaction mixture did not separate into layers. Analysis of the reaction mixture by gas chromatography showed that 73% of the acrolein was converted to acetal. When equimolar quantities of the reactants were used as in Example 2, separation of layers occurred and the conversion to acetal was 89%.

EXAMPLE 12

A mixture of 10.6 g. (.151 mole) of methacrolein and 14.4 g. (.138 mole) of 2,2-dimethyl-1,3-propanediol was stirred at 25°–40° C in the presence of 0.1% of hydrogen chloride based on the total weight of the reactants. Two layers separated in 10 minutes. The acetal layer (23.5 g.) contained 85.4% of the 2-(2-propenyl)-5,5-dimethyl-1,3-dioxane, 9.4% methacrolein, 1.6% water and 1.4% of the diol. The aqueous layer (2.89 g.) contained 75% water, 15% diol and 2% of methacrolein. Conversion of diol to acetal was 93.5%.

EXAMPLE 13

A mixture of 21.2 g. of formaldehyde (0.20 mole) and 18.0 g. of 1,3-butanediol (0.20 mole) was reacted in the presence of 0.1% hydrogen chloride based on the total weight of the reactants. The mixture separated into 2 layers — an aqueous layer of 5.1 g. and an acetal layer of 33.3 g. The aqeuous layer contained 53% of water and 44% of 1,3-butanediol. The acetal layer contained 1% water, 8.5% aldehyde and 90% 4-methyl-1,3-dioxane. The conversion to acetal was 82%.

It is to be understood that any of the components and conditions mentioned as suitable herein can be substituted for its counterpart in the foregoing examples and that although the invention has been described in considerable detail in the foregoing, such detail is solely for the purpose of illustration. Variations can be made in the invention by those skilled in the art without departing from the spirit and scope of the invention except as set forth in the claims.

What is claimed is:

1. In a process for preparing acetals by reacting diols with aldehydes the improvement which comprises reacting an alpha, beta diol; mixtures thereof; an alpha, gamma diol or mixtures thereof wherein said diol has 4 to 20 carbon atoms at a temperature ranging from 0°–100° C in the presence of an acid catalyst with from a stoichiometrically equivalent quantity to a 50% excess of an aldehyde having 1 to 4 carbon atoms to yield a liquid acetal having a solubility of less than 10% by weight in water at 25° C.

2. The improvement of claim 1 wherein the acid catalyst is a strongly acidic water insoluble ion exchange resin.

3. The improvement of claim 1 wherein the temperature ranges from 25° to 50° C.

4. The improvement of claim 1 wherein the alcohol is 2-methyl-1,3-propanediol.

5. The improvement of claim 1 wherein the aldehyde is acrolein.

6. The improvement of claim 1 wherein the acetal is a 1,3-dioxane.

7. The process of claim 1 wherein the aldehyde is selected from acetaldehyde, acrolein, propionaldehyde, methacrolein and formaldehyde.

* * * * *

UNITED STATES PATENT OFFICE
CERTIFICATE OF CORRECTION

PATENT NO. : 4,024,159
DATED : MAY 17, 1977
INVENTOR(S) : MARVIN L. PETERSON

It is certified that error appears in the above-identified patent and that said Letters Patent are hereby corrected as shown below:

Column 1, line 43, "$C_{alcohol}C_{aldehyde}$" should be -- $C_{alcohol} \cdot C_{aldehyde}$ --.

Column 8, line 46, after "claim" add -- 1 --.

Signed and Sealed this

Twenty-seventh Day of September 1977

[SEAL]

Attest:

RUTH C. MASON
Attesting Officer

LUTRELLE F. PARKER
Acting Commissioner of Patents and Trademarks